(12) United States Patent
Chen

(10) Patent No.: US 6,921,547 B2
(45) Date of Patent: Jul. 26, 2005

(54) EXTERNALLY APPLIED MEDICINE FOR BABY'S HERNIA

(76) Inventor: Ren-Rong Chen, No. 47, Chung Hsiao Street, Hualien (TW)

(*) Notice: Subject to any disclaimer, the term of this patent is extended or adjusted under 35 U.S.C. 154(b) by 155 days.

(21) Appl. No.: 10/653,896

(22) Filed: Sep. 4, 2003

(65) Prior Publication Data

US 2005/0053643 A1 Mar. 10, 2005

(51) Int. Cl.⁷ .................. A61K 35/78; A61K 35/64; A61K 9/70
(52) U.S. Cl. .................. 424/746; 424/443; 424/538; 424/757; 424/773
(58) Field of Search .................. 424/443, 725, 424/757, 746, 773, 538

(56) References Cited

U.S. PATENT DOCUMENTS 6,103,272 A * 8/2000 Keeney .................. 424/618

6,486,307 B1 * 11/2002 Gandhi et al. .................. 536/20

FOREIGN PATENT DOCUMENTS

| CN | 1341426 | * | 3/2002 |
| CN | 1485058 | * | 3/2004 |
| KR | 344361 | * | 7/2002 |

* cited by examiner

Primary Examiner—Christopher R. Tate
(74) Attorney, Agent, or Firm—Bacon & Thomas

(57) ABSTRACT

An externally applied medicine for treating pediatric hernia utilizes a dosage unit in powder form contained in a fabric pouch which is applied to the navel of a baby suffering from a hernia. The dosage unit is made from four ingredients which are ground to a powder. The ingredients include *Salvia chinensis* Benth; *Rehmannia glutinosa* Libosch; *Foeniculum vulgare* mill; and *Cryptotympana postulata* faba.

18 Claims, 1 Drawing Sheet

EXTERNALLY APPLIED MEDICINE FOR BABY'S HERNIA

BACKGROUND OF THE INVENTION

1. Field of the Invention

This invention pertains to the field of traditional Chinese medicine. More particularly the invention pertains to an externally or topically applied composition which includes herbal ingredients for treating hernias in babies, especially inguinal hernias in male babies.

2. Description of Related Art

Baby's hernia (pediatric hernias) is a type of enterocele and thus involves a portion of the intestine which protrudes through the abdominal wall. A significant number of full term babies may be born or may develop groin or inguinal hernias. Most hernias (about 80–90%) of this type occur in boys. The incidence of this type of hernia is higher in premature babies.

The occurrence of inguinal hernias in boys results from abnormalities during the development and descent of the testicles. The testicles develop within the abdominal cavity and during the third trimester of pregnancy they descend into the scrotum. They pass through the abdominal wall via the inguinal canal. Once they have arrived at their final destination in the scrotum, the inguinal canal should close. Occasionally the canal does not properly close and this failure to close may lead to herniation at this location.

A hernia in an infant or a child will appear as a bulge or a swelling in the groin. In boys the swelling generally appears in the scrotum and will thus have the appearance of testicular swelling.

In addition to inguinal hernias, pediatric hernias also include umbilical hernias which involve intestinal bulging through the abdominal wall at the umbilicus or navel. Umbilical hernias appear as bulges at the umbilicus or navel.

Surgery is generally required if the intestinal protrusion of the hernia cannot be reduced. In particular surgery is required to prevent strangulation of irreducible hernias.

Surgery is very risky and often results in complications which may include death. It would therefore be beneficial if nonsurgical methods of treatment were available to treat this condition.

In some instances support structures such as a fastening belt may be worn by the individual who suffers from the hernia. Such belts are designed to prevent the above-noted bulging. These supports are very inconvenient and are not desirable for infants. It would also be beneficial if treatment through the use of such supports could be eliminated.

SUMMARY OF THE INVENTION

It is an objective of this invention to provide a topically applied medicine for treating baby's hernia (pediatric hernia).

It is also an objective of this invention to provide a method for treating baby's hernia with an externally applied medicine.

The approach which the present invention takes to achieve the above-noted objectives conforms with traditional Chinese medicine (TCM) which is an integral part of the Chinese culture. Traditional Chinese medicine is a complete medical system which has been used for many centuries for the diagnosis, treatment and prevention of illness. According to traditional Chinese medicine, many factors must be brought into harmony and balance since disease is the result of these factors becoming out of balance or harmony with each other. The strategy of Chinese medicine is to restore harmony of these factors. These factors include cold and hot, wet and dry, etc.

Modern medicine in China includes TCM and Western medicine. In China, TCM is under the administration of state administration of TCM and pharmacology. In China, national strategies, law and regulations governing TCM are now in place to guide and promote the research and development in this field of technology.

TCM is defined as a medical science governing the theory and practice of traditional Chinese medicine. It includes Chinese medication, pharmacology/herbalogy, acupuncture, massage and Quigong. Hospitals in China are now classified as being specialized in Western medical systems, TCM or both.

Applicant has discovered that the above-noted objectives are obtained by formulating a topically applied medicine which comprises the following ingredients:

1) *Salvia chinensis* Benth
2) *Rehmannia glutinosa* Libosch
3) *Foeniculnm vulgare* mill
4) *Crytotympana postulata* faba Applicant has discovered (using techniques of traditional Chinese medicine) that the above-noted objectives can be met by the external application of a powder composition made from the above-identified ingredients. In this regard it is to be noted that according to traditional Chinese medicine, the hernias which are of particular interest in this invention involves testicular chillness and testicular weakness. The testicles are situated (in babies) about 3 inches below the navel. In the middle is Dang Tien Hilum which has one stream of oxygen through heart and testicles which circulates continuously. If the subject suffers from cold penetration or other factors, it will cause the testicles, intestine and Dang Tien Hilum to chill and weaken. It also involves weakening of intestinal functional and causes intestinal fat or oil to fall into the testicles and form the meatball which, according to traditional Chinese medicine is the hernia referred to above.

Using concepts of traditional Chinese medicine, applicant has discovered the following:

*Rehmannia glutinosa* Libosch and *Foeniculnm vulgare* mill are tonic materials. Their properties are aromatic, interpolating and mild and can enter into the testicles. They can also penetrate the intestine and bring more oxygen to the intestine. Thus they can increase metabolism and enhance immunization. *Salvia chinensis* Benth can remove bruises and generate new blood. Applicant uses the warm property of *Salvia chinensis* Benth to control cold so that the testicles and intestine can get warmth. Once the intestine has been restored to its smooth functioning, fat and oil will go back to its original position. Therefore the redundant meat of the hernia will vanish spontaneously through the use of this invention. Consequently, there is no abdominal pain and thus crying of the baby is minimized.

The topically applied composition which is used in the present invention is obtained by grinding the above-noted four ingredients to form a powder which can be topically applied on the baby's abdomen, in particular on the baby's navel or bellybutton. Preferably the powder containing the four ingredients is formulated into a dosage unit containing about 3.5 grams of the powder. The powder is advantageously placed into a pouch which has small holes therein to allow the powder to come in contact with the baby's skin. Preferably the pouch is made from conventional fabric (woven or unwoven). Conventional fabrics inherently contain small openings which allow the powder to come in contact with the patient's skin.

Treatment comprises repeated applications of the composition to the patient. Preferably one dosage unit in the form of a two sided pouch is applied over the navel and is kept at this location for a first treatment period (e.g., about 12 hours). The first treatment period may utilize one side of the pouch. After a rest period (e.g., about 12 hours), the pouch is reapplied for a second treatment period (e.g., also about 12 hours). The second treatment period may use the second or unused side of the pouch or, alternatively, the second treatment period may use a new pouch. A plurality of dosage units are applied to the patient. Typically the patient can get well after 2–3 doses to 5–6 doses in two or three days.

DETAILED DESCRIPTION OF THE INVENTION AND PREFERRED EMBODIMENTS

The composition of the present invention includes all four of the above-noted ingredients as the active component. No other ingredients are required. Preferably the composition contains an equal amount of each of the four ingredients (i.e., 25% by weight of each of the four ingredients or one part by weight of each of the four ingredients). However, it is not essential that the composition must contain an equal amount by weight of each of the four ingredients. The composition may include the four ingredients in the following amounts:

1) 0.92 to 0.83 parts by weight of *Salvia chinensis* Benth;

2) 0.92 to 0.83 parts by weight of *Rehmannia glutinosa* Libosch;

3) 0.92 to 0.83 parts by weight of *Foeniculnm vulgare* mill; and 4) 0.92 to 0.83 parts by weight of *Crytotympana postulata* faba.

The composition is preferably formulated into dosage units of the powder which can vary in weight from 3.68 grams to 3.32 grams per dosage unit. The preferred dosage unit is 3.5 grams with each ingredient contained therein in an equal amount.

Figure 1:
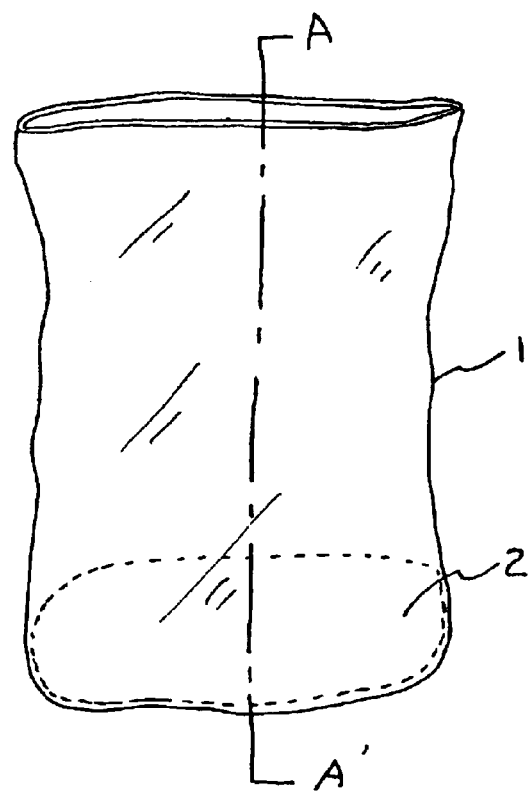
FIG. 1 illustrates an embodiment of a dosage unit according to the present invention which comprises a fabric pouch containing one dosage unit of the invention.
Figure 2:
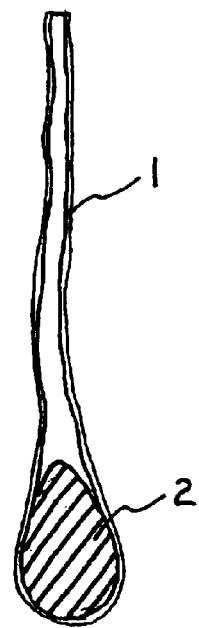
FIG. 2 is a cross-section of FIG. 1 taken along line A–A'.

Each dosage unit is preferably contained in a fabric pouch (e.g., cheesecloth or similar open woven fabric with small openings therein). FIGS. 1 and 2 illustrate a dosage unit 2 contained in pouch 1. The dosage unit 2 is 3.5 grams of a powder made by pulverizing an equal amount of the four above-listed ingredients. The pouch which includes open end 3 may be closed by sewing it closed or by folding over the open end.

The composition of the invention is topically applied to the abdomen, preferably the navel or bellybutton. In order to keep the powder in place, it is convenient to place the powder in the pouch as described above. The pouch, containing a dosage unit, is applied to the navel and held in place for a first treatment period of time. After a rest period, a pouch containing a dosage unit is reapplied to the patient's navel where it is held in place for a second treatment period of time. The first treatment period, the second treatment period and the rest period may be approximately 12 hours although longer and shorter periods of time are permissible for the rest period and the treatment periods.

The second treatment period may utilize a fresh pouch or bag of medicine. However, it is advantageous to use one side of the pouch for the first treatment period and then use the second side of the pouch for the second treatment period. After the second treatment period, a new or fresh pouch of medicine is used for subsequent treatment periods. Alternating treatment periods and rest periods are utilized until the hernia disappears.

In a preferred embodiment one side of the pouch of medicine is applied for 12 hours for a first treatment period. The first treatment period is followed by a rest period of about 12 hours. On day 2 the second side of the pouch of medicine is applied for 12 hours which constitutes a second period of treatment. The second period of treatment is followed by a rest period which lasts for about 12 hours. On the third day a fresh pouch of medicine is utilized in the same manner that the first pouch was utilized on days 1 and 2. This procedure is repeated an effective number of times until the hernia disappears (i.e., is reduced).

The rest periods are desirable for the baby's comfort during the time frame during which treatment takes place. However, the time periods for the rest treatment may be reduced or eliminated. Thus, it is only essential to apply the composition of this invention to the patient's abdomen, preferably applying it to the patient's navel, for a period of time until the hernia disappears.

The composition of the invention is advantageously divided into a first potion and a second potion. These first and second potions are appropriately used according to the patient's condition. Typically, after using about three pouches of the first potion, the swelling of the testicles will vanish. At this point it is desirable to use three pouches of the second potion. After using about three pouches of the second potion, loose skin around the testicles becomes tighter and the testicles regain their original shape, thus indicating reduction of the hernia. Both potions may be the same.

After using the pouches of the medicine as described above, it has been observed that:

1) the mild soft ball on the testicle will naturally vanish 2) after vanishing of the mild soft ball on the testicle, a loose layer of skin around the testicle appears (skin of the scrotum)

3) when the loose layer of skin around the testicles tightens, full recovery is indicated.

The best time to apply the pouches of medicine is in the evening after bathing. When using the pouch of medicine, it is best to have the baby lie down and be hugged to reduce anxiety. The pouch of medicine exerts the most effective function for those babies whose age is under one year. For patients from age one to sixteen, the effectiveness of this medicine is reduced. However, if treatment is begun at an early stage and if the patients are able to rest during the treatment regimen, the treatment may be effective to cure hernias in patients of this age group. Treatment is also effective for adults and older people if the treatment is commenced at an early stage.

The first ingredients used in the composition is *Salvia chinensis* Benth. This is a well known herbal medication. Its properties are bitter taste, astringency, mild, cold and non-toxic. The main active ingredient is Scutellarin. *Salvia*

*chinensis* Benth and the above-noted main ingredient is useful for treating fatigue caused by anemia, uterine bleeding, irregular menses, abdominal pain, hernia colic, and joint pain. *Salvia chinensis* Benth can also be used to treat lymphatic swelling, carbuncles and mastitis. It is effective in discharging pus and encourages tissue regeneration.

The second ingredient is *Rehmannia glutinosa* Libosch. Its properties are sweet taste, cold and non-toxic. The root of this plant contains mannite (also known as manitol; $C_6H_{14}O_6$), rehmanin and sugar. It also contains iron and thus qualifies as a tonic and strength medicine. *Rehmannia glutinosa* Libosch functions to nourish the blood and provide heart stimulation in weak individuals. It is also a medicine which is useful to stop bleeding for hemoptysis, hematemesis and uterine bleeding. It is known to cure moist hot caused by TB and is effective for blood sugar repression, heart stimulation and diuresis. It is also known that this ingredient may be used to treat DM (Diabetes Mellitus), anemia, general weakness and may be used to treat patients having a tendency to hemorrhage.

The third ingredient is *Foeniculnm vulgare* mill. This ingredient is pungent, fragrant, sweet and non-toxic. *Foeniculnm vulgare* mill contains 3–8% anethole. The fruit of *Foeniculnm vulgare* mill contains 3% essence oil which contains 50–60% anethole and Fenchone fat, oil and starch. *Foeniculnm vulgare* mill is a medicine which is used to promote stomach health and for cold expelling. It is effective in sputum repression, milk hastening, gastroenteric hernia pain, intestinal bloating and abdominal bulge. It is also useful to treat lumbar pain and indigestion.

The fourth ingredient is *Cryptotympana pustulata* Faba which belongs to the insect category since this ingredient is the exuviae produced by the exuviation of cicada. In other words this ingredient is the exoskeleton of cicada produced when cicada molt. Its properties are salty taste, cold, sweet and non-toxic. It may be used as an anti-fever or anti-convulsion medicine. It is also useful to treat febrile headache, febrile seizures, convulsions, cramps, puerperal fever and tetanus convulsions. It may also be used to treat laryngitis, soundless caused by cough, rash, skin itching, cataracts, middle ear inflammation and tonsilitis. It can also cure eye diseases owing to congestion, redness and astringency and photophobia.

The first three ingredients are herbal while the fourth ingredient, being obtained from cicada shells or exoskeletons which are molted by the cicada, is an insect derived ingredient.

Each of the herbal ingredients are obtained from particular parts of a plant. The plants are mature plants and may be grown under any cultivation conditions which are suitable for the growth and propagation of the plants and which are well known to those skilled in the art. They can be grown in conventional potting soil under ambient conditions to produce the plant parts which are useful in this invention.

Each of the aforementioned herbal ingredients require the selection of a particular part of the plant.

The root of the *Salvia chinensis* Benth is utilized in this invention for the first herbal ingredient. The root is generally about one meter long. Thus it is advantageous to use a plant which is old enough to produce a root of this size although smaller and larger roots may be used.

The second ingredient is the root of *Rehmannia glutinosa* Libosch. The root is steamed and sun-dried.

The third ingredient is the seed of *Foeniculnm vulgare* mill. These are relatively small seeds which resemble wheat seeds in size.

The fourth ingredient is the molted shell (i.e., exoskeleton) of cicada. The shells are preferably washed with boiling water to remove dirt and cook the shells. The cooked shells are dried such as by sun drying prior to use.

By treating a baby with the composition described herein, it is not necessary to use other medications. Furthermore, the baby will not need other treatments such as acupuncture and surgery. In addition, the use of a fastening belt to aid in the reduction of the hernia is not required. Furthermore, there are no known complications for the treatment of this invention and the baby can eat and sleep well during the treatment process. Using this medicine increases intestinal oxygen and smooth blood circulation and therefore increases intestinal peristalsis and immunity so that the intestine can naturally contract and go back to its original location. At the same time this medicine can lubricate the intestine so that edema will disappear spontaneously and the patient will get well.

What is claimed is:

1. A composition for the external or topical treatment of a hernia in a human being, said composition being a mixture which comprises the following four ingredients in powder form:

root of *Salvia chinensis* Benth;
   root of *Rehmannia glutinosa* Libosch;
   seed of *Foeniculum vulgare* mill; and
   exoskeleton of cicada.

2. The composition of claim 1 wherein each of the four ingredients are present in an amount of about 0.92 to 0.83 parts by weight.

3. The composition of claim 2 wherein each of the four ingredients are present in about equal amounts by weight.

4. The composition of claim 3 which is formulated into a dosage unit of about 3.68 to about 3.32 grams.

5. The composition of claim 4 wherein the dosage unit is about 3.5 grams.

6. The composition of claim 4 wherein said dosage unit is contained within a pouch.

7. The composition of claim 6 wherein said pouch is made from fabric.

8. A method for treating a human being afflicted with a hernia which comprises externally applying a medicinal composition to the abdomen or navel of said human being; said medicinal composition being a mixture which comprises the following four ingredients in powder form:

root of *Salvia chinensis* Benth;
   root of *Rehmannia glutinosa* Libosch;
   seed of *Foeniculum vulgare* mill; and
   exoskeleton of cicada.

9. The method of claim 8 wherein said human is one year old or less.

10. The method of claim 9 wherein each of the four ingredients are present in an amount of about 0.92 to 0.83 parts by weight.

11. The method of claim 10 wherein each of the four ingredients are present in about equal amounts by weight.

12. The method of claim 11 wherein said medicinal composition is in the form of a dosage unit of about 3.68 to about 3.32 grams.

13. The method of claim 12 wherein said dosage unit is about 3.5 grams.

14. The method of claim 12 wherein said dosage unit is contained within a pouch.

15. The method of claim 14 wherein said pouch is made from fabric.

16. The method of claim 8 wherein said medicinal composition is contained within a pouch and a plurality of said pouches containing said medicinal composition therein are sequentially applied, one at a time, to the abdomen or navel of said human being.

17. The method of claim 16 wherein each of the four ingredients of said medicinal composition are present in about equal amounts by weight in a dosage unit of about 3.32 grams to about 3.68 grams.

18. The method of claim 17 wherein each pouch remains in contact with said abdomen or navel for about 12 hours with a rest period of about 12 hours between the application of each pouch.

* * * * *